United States Patent
Hasegawa

(10) Patent No.: US 7,967,755 B2
(45) Date of Patent: *Jun. 28, 2011

(54) ULTRASONIC PROBE

(75) Inventor: Yasunobu Hasegawa, Saitama (JP)

(73) Assignee: Nihon Dempa Kogyo Co., Ltd., Tokyo (JP)

( * ) Notice: Subject to any disclaimer, the term of this patent is extended or adjusted under 35 U.S.C. 154(b) by 777 days.

This patent is subject to a terminal disclaimer.

(21) Appl. No.: 11/879,909

(22) Filed: Jul. 19, 2007

(65) Prior Publication Data

US 2008/0027326 A1      Jan. 31, 2008

(30) Foreign Application Priority Data

Jul. 25, 2006   (JP) ................................. 2006-201513

(51) Int. Cl.
*A61B 8/14*       (2006.01)
*H01L 41/00*    (2006.01)

(52) U.S. Cl. ...................................... 600/459; 310/334

(58) Field of Classification Search .................. 600/437, 600/459; 310/334
See application file for complete search history.

(56) References Cited

U.S. PATENT DOCUMENTS

| | | | |
|---|---|---|---|
| 4,426,886 A * | 1/1984 | Finsterwald et al. | 73/633 |
| 7,554,245 B2 * | 6/2009 | Hasegawa | 310/334 |
| 2003/0055338 A1 * | 3/2003 | Steininger et al. | 600/459 |
| 2003/0229287 A1 | 12/2003 | Flesch et al. | |

FOREIGN PATENT DOCUMENTS

| | | |
|---|---|---|
| DE | 3405537 A1 | 8/1985 |
| EP | 0 223 724 A | 8/1987 |
| JP | 7-38851 | 5/1995 |
| JP | 2003-175033 | 6/2003 |
| JP | 2006-346125 | 12/2006 |

OTHER PUBLICATIONS

European Search Report dated Jul. 14, 2008.

* cited by examiner

*Primary Examiner* — Michael T Rozanski
(74) *Attorney, Agent, or Firm* — Scott D. Wofsy; Edwards Angell Palmer & Dodge LLP

(57) ABSTRACT

The present invention relates to an ultrasonic probe comprising a group of piezoelectric elements consisting of a plurality of piezoelectric elements of a narrow card shape arrayed in a long-axis direction thereof and a rotational mechanism that rotates and oscillates said group of piezoelectric elements to the left and right in a short-axis direction thereof about the center of said long-axis direction; wherein said rotational mechanism is provided with a first bevel gear having teeth in at least an arc shape, a second bevel gear meshing with said first bevel gear and rotating in the horizontal direction, and a drive motor that rotates said second bevel gear; and also at least one of said first bevel gear and said second bevel gear is made of a synthetic resin.

2 Claims, 2 Drawing Sheets

ULTRASONIC PROBE

BACKGROUND OF THE INVENTION

The present invention relates to an ultrasonic probe in which a group of piezoelectric elements that is a source of ultrasonic waves oscillates in the short-axis direction to obtain a three-dimensional image (hereinafter called a "short-axis oscillating probe") and, in particular, to a short-axis oscillating probe of a simple configuration in which the operational noise of the probe while operating is minimized to remove that source of discomfort to the patient.

1. Field of the Invention

A short-axis oscillating probe that is known in the art obtains a three-dimensional image by electronically scanning a group of piezoelectric elements in the long-axis direction of the probe and also by mechanically scanning (oscillating) the group of piezoelectric elements in the short-axis direction thereof (see Japanese Patent Laid-Open Publication 2006-346125 (prior-art example 1), Japanese Patent Publication No. TOKKO-HEI 7-38851 (prior-art example 2), and Japanese Patent Laid-Open Publication No. 2003-175033 (prior-art example 3)). Since components such as wiring (connective wires) and scan circuitry of this type of short-axis oscillating probe can be configured simply, in comparison with a matrix type of probe in which piezoelectric elements are arrayed horizontally and vertically to provide a two-dimensional electronic scan, this probe can be implemented easily.

2. Description of Related Art

A prior-art example of a short-axis oscillating probe is shown in FIG. 2, where FIG. 2A is a section taken along the long-axis direction thereof and FIG. 2B is a section taken along the short-axis direction thereof.

The short-axis oscillating probe of this prior-art example is provided with a group of piezoelectric elements 1 and a rotational mechanism 2, as shown in FIG. 2A. The group of piezoelectric elements 1 is arrayed on a backing member (not shown in the figure), with the widthwise direction of a plurality of card-shaped piezoelectric elements 1a aligned in the long-axis direction and also the lengthwise direction thereof aligned in the short-axis direction. The backing member is affixed to the top of a base 4, which is formed in a convex dome shape in the long-axis direction, with the configuration being such that the group of piezoelectric elements 1 is curved outward in the long-axis direction.

A flexible substrate 5 that has been connected electrically to the group of piezoelectric elements 1 over the entire region of the probe in the long-axis direction thereof is lead out downward from one end side of the probe in the short-axis direction. In this case, a conductive path 5a of the flexible substrate 5 is connected electrically to a drive electrode of each piezoelectric element 1a. The two could be connected directly, as shown in FIG. 2, or the drive electrode of each piezoelectric element 1a could be connected indirectly to the conductive path 5a by means such as silver foil and conductive wiring.

The rotational mechanism 2 shown in FIG. 2 comprises a retaining plate 6, a case 7, a first bevel gear 8a, a second bevel gear 8b, a rotational shaft 9, and a drive motor 10 that has been attached to a framing member 7b. The retaining plate 6 has leg portions 6a and 6b on the lower surface thereof on both edge sides in the long-axis direction, and the base 4 holding the group of piezoelectric elements 1 is affixed to the upper surface thereof. Center shafts 11a and 11b that penetrate through the corresponding leg portions 6a and 6b are provided in the long-axis direction (on the line X-X in the horizontal direction shown in FIG. 2A), on bearings 11c and 11d.

The leg portions 6a and 6b are provided to be freely rotatable with respect to the center shafts 11a and 11b.

The case 7 is formed to be concave in section with the upper surface thereof being open, and projecting ends of the center shafts 11a and 11b that protrude from the leg portions 6a and 6b are connected (affixed) to peripheral walls of the case 7. A slit 12 is formed in the long-axis direction of the bottom wall of the case 7, and the flexible substrate 5 from the group of piezoelectric elements 1 is lead out to the exterior therethrough. A material such as a synthetic resin 13 is embedded in the slit 12 to seal the same.

The first bevel gear 8a is provided on the inner surface of the leg portion 6a, below the center shafts 11a and 11b, and has teeth in an arc (a fan shape) with a peak thereof at the lower end in the vertical direction. The second bevel gear 8b is borne on the free end side of the rotational shaft 9, which is in the vertical direction perpendicular to the center shafts 11a and 11b (the line X-X), and engages with the first bevel gear 8a to rotate in the horizontal direction (the X-X direction). The rotational shaft 9 is lead out from the bottom wall of the case 7 and is sealed by sealing 14, and the other end thereof is linked (meshes) with the drive motor 10 by means such as metal gears 15a and 15b.

In this prior-art example 1, the first bevel gear 8a and the second bevel gear 8b are formed of metal, and the diameter of the equivalent circle of the arc-shaped teeth of the first bevel gear 8a is greater than the diameter of the second bevel gear 8b. In addition, the diameter of the metal gear 15a affixed to the rotational shaft 9 is greater than the diameter of the metal gear 15b of the drive motor 10.

By making the gear ratio from the drive motor 10 to the first bevel gear 8a greater in this manner, this configuration ensures that the rotational force (torque) of the drive motor 10 is increased and maintained in the transmission of drive to the first bevel gear 8a. Note that a cover (not shown in the figure) that encloses the group of piezoelectric elements 1 is provided for the case 7, the group of piezoelectric elements 1 and other components are hermetically sealed therein, and the interior of the case is filled with an ultrasound transmission medium such as oil.

In the thus-configured prior-art example, the rotation (oscillation) of the second bevel gear 8b that configures the rotational mechanism 2 horizontally to left and right causes the first bevel gear 8a to oscillate with respect to the vertical plane so that the peak thereof inclines upward to the left or right from the center. In other words, the peak of the first bevel gear 8a rotates and oscillates to the left and right of the vertical direction acting as center. Thus the leg portions 6a and 6b of the retaining plate 6 rotate and oscillate to the left and right with respect to the center shafts 11a and 11b, and also the group of piezoelectric elements 1 rotate and oscillate to the left and right in the short-axis direction, in the opposite directions thereto. In addition, the rotational angle in the short-axis direction from a reference position is detected by a rotational angle detection mechanism (not shown in the figure) for the rotational shaft 9, thus obtaining information from an object to be detected (organism).

Problems with Prior Art

However, in the above described example of a short-axis oscillating probe of the art, the first bevel gear 8a, the second bevel gear 8b, and also the metal gears 15a and 15b emit characteristic metallic noises when they engage because they are all made of metal, which raises a problem in that it causes discomfort to the doctor (operator) and, in particular, to the patient during operation.

Note that in the generation of metallic noise is removed in abovementioned prior-art example 3, because the motor and the rotational axis on the piezoelectric element side are directly driven by a pulley linkage using a belt. In such a case, however, there is no two-stage linkage using bevel gears in addition to the gear that is connected directly to the drive motor, as described above, so it is necessary to increase the diameter ratio of the pulleys to ensure that the rotational force of the motor is transferred reliably to the piezoelectric element side. Since the pulley on the piezoelectric element side is thus increased in size, it is difficult to design a compact probe.

In contrast thereto, the configuration of the above-described prior-art example 1 employs a two-stage linkage using the gear linkage of the metal gears 15a and 15b together with the first bevel gear 8a and second bevel gear 8b to transfer the driving force of the drive motor 10, so that the metal gears 15a and 15b, the first bevel gear 8a, and the second bevel gear 8b can be made smaller. This facilitates a compact design.

An objective of the present invention is to provide an ultrasonic probe in which the generation of metallic noise by the meshing of gears is suppressed, making it possible to remove a source of discomfort to the operator and the patient.

SUMMARY OF THE INVENTION

The present invention relates to an ultrasonic probe comprising a group of piezoelectric elements consisting of a plurality of piezoelectric elements of a narrow card shape arrayed in a long-axis direction thereof and a rotational mechanism that rotates and oscillates said group of piezoelectric element to the left and right in a short-axis direction thereof about the center of said long-axis direction; wherein said rotational mechanism is provided with a first bevel gear having teeth in at least an arc shape, a second bevel gear meshing with said first bevel gear and rotating in the horizontal direction, and a drive motor that rotates said second bevel gear; the rotational axis of said second bevel gear and said drive motor are linked by a pulley linkage using a belt; and also at least one of said first bevel gear and said second bevel gear is made of a synthetic resin.

Since this configuration ensures that there is a pulley linkage using a belt between the rotational shaft of the second bevel gear and the drive motor, and at least one of the first bevel gear and the second bevel gear is made of a synthetic resin, there is no engagement between metals and thus there is no generation of the characteristic metallic noise during rotation. This makes it possible to remove a source of discomfort to the operator and, in particular, to the patient.

BRIEF DESCRIPTION OF THE DRAWINGS

FIG. 2 is illustrative of a prior-art example of a short-axis oscillating probe, where

DETAILED DESCRIPTION OF PREFERRED EMBODIMENT

Figure 1:
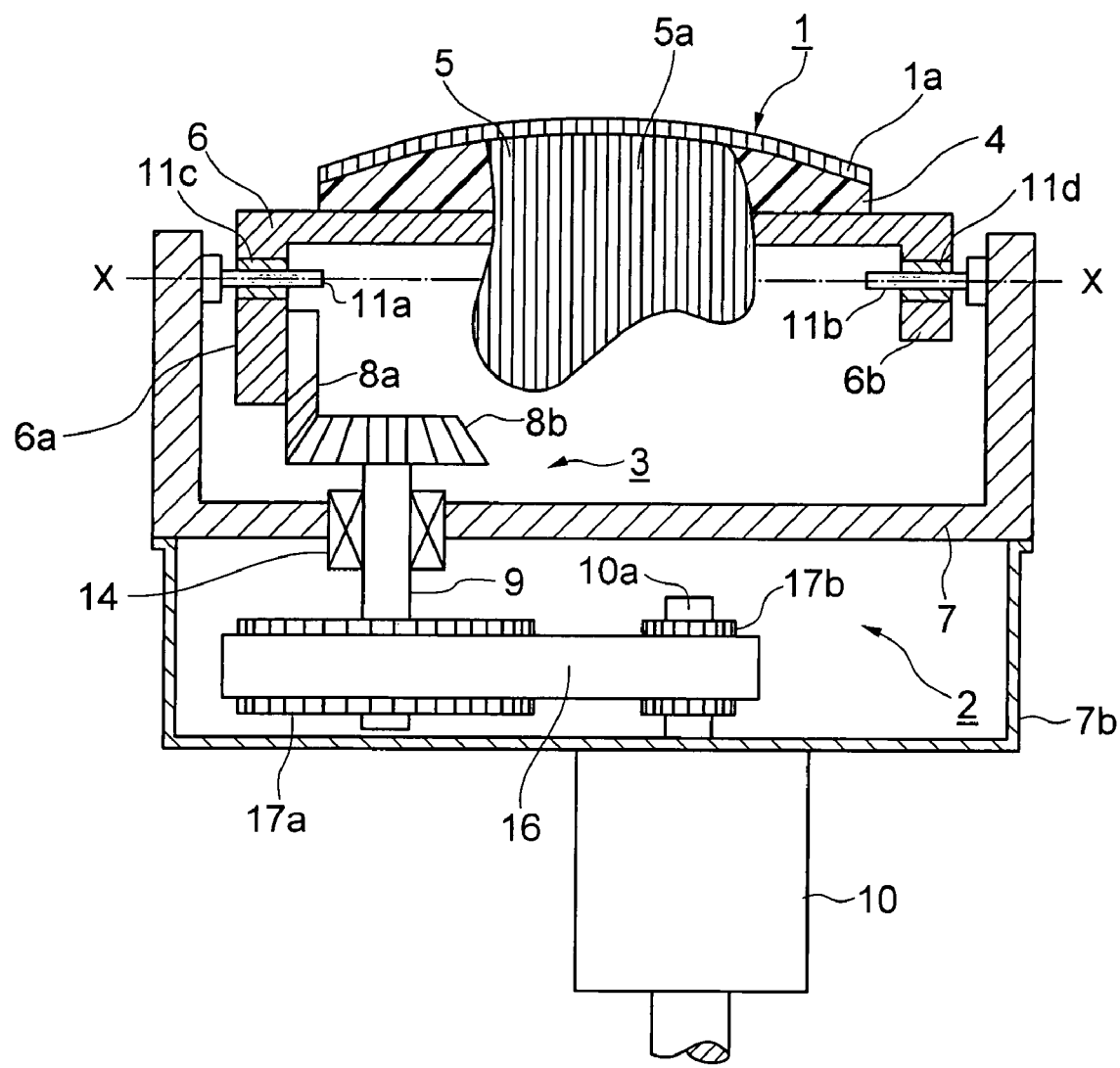
FIG. 1 is a section taken in the long-axis direction, illustrating an embodiment of the short-axis oscillating probe of the present invention.
Figure 2A:
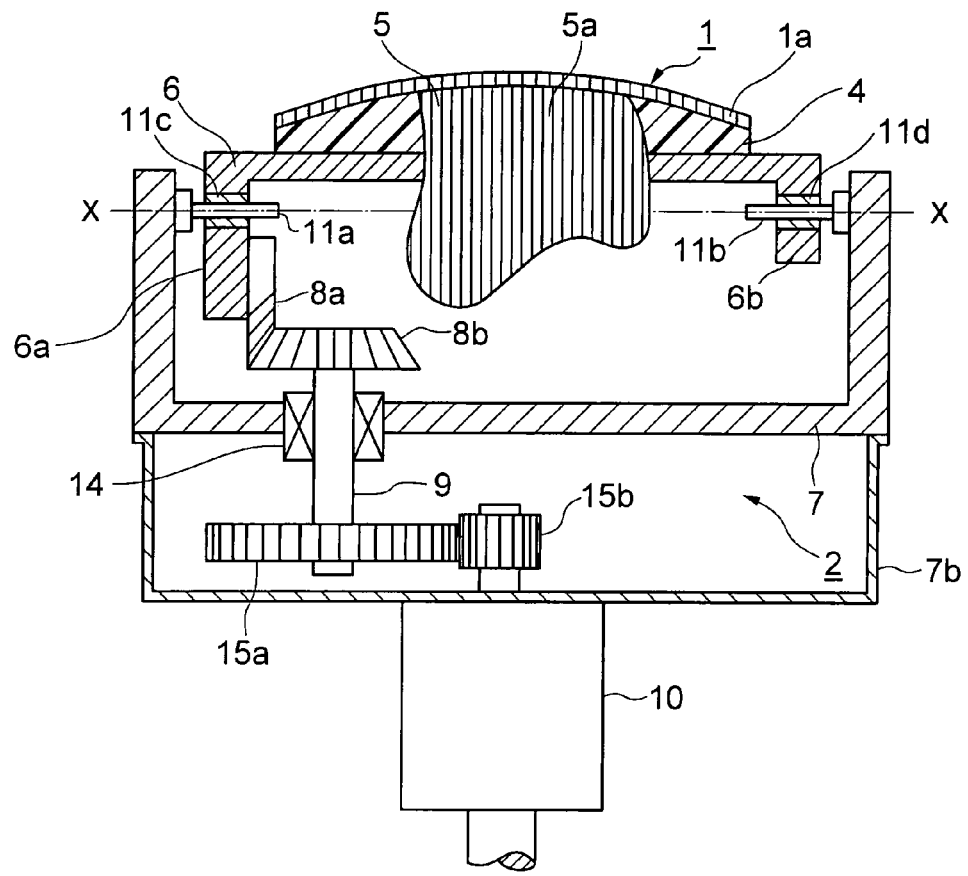
FIG. 2A is a section taken in the long-axis direction thereof and FIG. 2B is a section taken in the short-axis direction thereof.
Figure 2B:
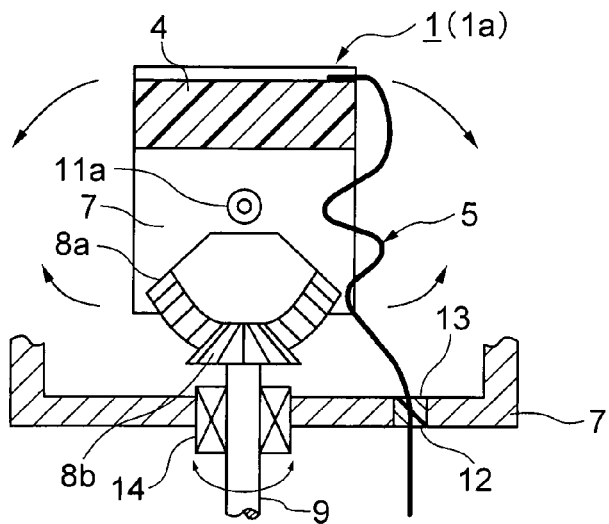

A section taken in the long-axis direction through an embodiment of the short-axis oscillating probe of the present invention is shown in FIG. 1.

The short-axis oscillating probe of the present invention is provided with the group of piezoelectric elements 1 and the rotational mechanism 2. The group of piezoelectric elements 1 are arranged in a convex form on a backing member (not shown in the figure) that is attached to an upper surface of the base 4, with the widthwise direction of a large number of piezoelectric elements 1a arranged in the long-axis direction thereof, and the flexible substrate 5 that provides electrical connections with the group of piezoelectric elements 1 through the conductive path 5a is lead out from one end side in the short-axis direction.

The rotational mechanism 2 is formed of the retaining plate 6 with the group of piezoelectric elements 1 affixed to the upper surface thereof; the case 7 of an indented shape and having the center shafts 11a and 11b, which rotate freely in the leg portions 6a and 6b of the retaining plate 6 and engage smoothly with the bearings 11c and 11d; the first bevel gear 8a, which is provided in one leg portion 6a of the retaining plate 6 and which has teeth in an arc shape; the second bevel gear 8b, which meshes with the first bevel gear 8a and which has the rotational shaft 9 that is led out from the bottom wall of the case 7; and the drive motor 10 attached to the framing member 7b.

In this case, the first bevel gear 8a on the driven side is formed of a synthetic resin and the second bevel gear 8b on the drive side is formed of a metal. In addition, the rotational shaft 9 of the second bevel gear 8b and a rotational axis 10a of the drive motor 10 are linked by a pulley linkage using a belt 16.

In this case, the diameter of the first bevel gear 8a is larger than that of the second bevel gear 8b, a pulley 17a on the rotational shaft 9 is larger than a pulley 17b of the drive motor 10 (the gear ratio thereof is larger), and thus the rotational force of the motor is increased. Uneven grooves are provided in the pulleys 17a and 17b and the belt 16, and mutually meshing timing pulleys and a timing belt are used therefor.

Since this configuration ensures that the connection between the rotational shaft 9 of the second bevel gear 8b and the rotational axis 10a of the drive motor 10 is by a pulley linkage using the belt 16, the driving force can be transferred reliably and there is no metallic noise generated by the meshing of the metal gears 15a and 15b as in the prior-art example. In addition, since the first bevel gear 8a is formed of a synthetic resin and the second bevel gear 8b is formed of a metal, any metallic noise generated when those gears engage can be minimized. Thus the generation of metallic noise during operation is suppressed, thereby making it possible to remove a source of discomfort to the operator and, in particular, to the patient.

What is claimed is:

1. An ultrasonic probe comprising:
   a group of piezoelectric elements consisting of a plurality of piezoelectric elements of a narrow card shape arrayed in a long-axis direction thereof and a rotational mechanism that rotates and oscillates said group of piezoelectric elements to the left and right in a short-axis direction thereof about the center of said long-axis direction;
   wherein said rotational mechanism is provided with a first bevel gear having teeth in at least an arc shape wherein the first bevel gear is fabricated from metal, a second bevel gear meshing with said first bevel gear and rotating in the long-axis direction wherein the second bevel gear is fabricated from a synthetic resin, first and second pulleys each provided with uneven grooves and a drive motor that rotates said second bevel gear via said first and second pulleys;

the rotational axis of said second bevel gear and the rotational axis of said drive motor are linked by the first and second pulleys using a belt mutually meshing with the uneven grooves of the first and second pulleys.

2. An ultrasonic probe comprising:

a group of piezoelectric elements consisting of a plurality of piezoelectric elements arrayed in a long-axis direction thereof;

a rotational mechanism operative to rotate and oscillate the group of piezoelectric elements wherein said rotational mechanism includes:

a first bevel gear fabricated from metal, a second bevel gear fabricated from a synthetic resin, the second bevel gear meshing with the first bevel gear and rotating in the long-axis direction, first and second spaced apart pulleys each provided with uneven grooves;

a belt coupled between the first and second spaced apart pulleys configured to mesh with the uneven grooves of the first and second pulleys; and a drive motor that rotates the second bevel gear via the first and second pulleys.

\* \* \* \* \*